US011517029B2

United States Patent
Leulier et al.

(10) Patent No.: US 11,517,029 B2
(45) Date of Patent: Dec. 6, 2022

(54) PROBIOTIC COMPOSITION MAKING IT POSSIBLE TO PROMOTE JUVENILE LIVESTOCK GROWTH

(71) Applicants: ECOLE NORMALE SUPERIEURE DE LYON, Lyons (FR); CENTRE NATIONAL DE LA RECHERCHE SCIENTIFIQUE, Paris (FR); UNIVERSITE CLAUDE BERNARD LYON 1, Villeurbanne (FR)

(72) Inventors: Francois Leulier, Solaize (FR); Martin Schwarzer, Solaize (FR)

(73) Assignees: ECOLE NORMALE SUPERIEURE DE LYON, Lyons (FR); CENTRE NATIONAL DE LA RECHERCHE SCIENTIFIQUE, Paris (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 143 days.

(21) Appl. No.: 16/077,050

(22) PCT Filed: Feb. 10, 2017

(86) PCT No.: PCT/EP2017/052982
§ 371 (c)(1),
(2) Date: Aug. 10, 2018

(87) PCT Pub. No.: WO2017/137547
PCT Pub. Date: Aug. 17, 2017

(65) Prior Publication Data
US 2019/0350223 A1    Nov. 21, 2019

(30) Foreign Application Priority Data

Feb. 12, 2016   (FR) ...................................... 1651170

(51) Int. Cl.
| A23K 10/18 | (2016.01) |
| A23K 50/40 | (2016.01) |
| A23K 50/50 | (2016.01) |
| A23K 50/60 | (2016.01) |
| A23K 50/80 | (2016.01) |
| A23L 33/135 | (2016.01) |
| C12N 1/20 | (2006.01) |
| C12R 1/25 | (2006.01) |
| C12R 1/245 | (2006.01) |

(52) U.S. Cl.
CPC ............ *A23K 10/18* (2016.05); *A23K 50/40* (2016.05); *A23K 50/50* (2016.05); *A23K 50/60* (2016.05); *A23K 50/80* (2016.05); *A23L 33/135* (2016.08); *C12N 1/20* (2013.01); *C12N 1/205* (2021.05); *A23Y 2220/17* (2013.01); *A23Y 2220/35* (2013.01); *A23Y 2220/63* (2013.01); *A23Y 2220/67* (2013.01); *A23Y 2220/73* (2013.01); *C12R 2001/245* (2021.05); *C12R 2001/25* (2021.05)

(58) Field of Classification Search
None
See application file for complete search history.

(56) References Cited

U.S. PATENT DOCUMENTS

2017/0080034 A1    3/2017 Leulier et al.

FOREIGN PATENT DOCUMENTS

| EP | 2 768 312 | 8/2014 |
| FR | 2 877 811 | 5/2006 |
| WO | WO 2015/173386 | 11/2015 |

OTHER PUBLICATIONS

Agustina et al., J. Nutrition 143: 1184-1193 (2013).*
Hou et al., Gut Microbes 12(1): e1736974 (2020).*
Zhang et al., J. South China Agriculture Univ. 3: 81-84 (2006).*
Aleksandrzak-Piekarczyk, T. et al. "Genome Sequence of the Probiotic Strain *Lactobacillus rhamnosus* (Formerly *Lactobacillus easei*) LOCK900" *Genome Announcements*, Aug. 15, 2013, pp. 1-2, vol. 1, Issue 4.
Agustina, R. et al. "Probiotics *Lactobacillus reuteri* DSM 17938 and *Lactobacillus casei* CRL 431 Modestly Increase Growth, but Not Iron and Zinc Status, among Indonesian Children Aged 1-6 Years" *The Journal of Nutrition, American Society of Nutrition*, Jul. 1, 2013, pp. 1184-1193, vol. 143, No. 7.
Baah, J. et al. "Impact of a mixed culture of *Lactobacillus casei* and *L. lactis* on in vitro ruminal fermentation and the growth of feedlot steers fed barley-based diets" *Canadian Veterinary Journal—Revue Veterinaire Canadienne*, Jun. 1, 2009, pp. 263-271, supp. p. 1, vol. 89, No. 2.
Bernardeau, M. et al. "Safety and efficacy of probiotic lactobacilli in promoting growth in post-weaning Swiss mice" *International Journal of Food Microbiology*, Jul. 1, 2002, pp. 19-27, vol. 77, Nos. 1-2.
Chiofalo, V. et al. "Effects on the administration of *Lactobacilli* on body growth and on the metabolic profile in growing Maltese goat kids" *Reproduction Nutrition Development*, Sep. 1, 2004, pp. 449-457, vol. 44, No. 5.
Kankainen, M. et al. "Comparative genomic analysis of *Lactobacillus rhamnosus* GG reveals pili containing a human-mucus binding protein" *PNAS*, Oct. 6, 2009, pp. 17193-17198, vol. 106, No. 40.
Kim, E-K. et al. "Draft Genome Sequence of *Lactobacillus plantarum* Strain WJL, a *Drosophila* Gut Symbiont", *Genome Announcements*, Nov. 21, 2013, p. 1, vol. 1, Issue 6.

(Continued)

*Primary Examiner* — Erin M. Bowers
(74) *Attorney, Agent, or Firm* — Saliwanchik, Lloyd & Eisenschenk

(57) ABSTRACT

The probiotic composition comprises at least one lactic acid bacteria strain, preferably *Lactobacillus* with intestinal tropism, for use in promoting juvenile growth in livestock, with stimulation of linear growth and/or of IGF-1 level. Exemplary lactic acid bacteria include *Lactobacillus plantarum*, *Lactobacillus fermentum*, *Lactobacillus casei*, *Lactobacillus paracasei* and *Lactobacillus rhamnosus*. The strains can be selected in a mouse model. The invention also relates to a probiotic treatment method using this composition.

13 Claims, No Drawings

(56) References Cited

OTHER PUBLICATIONS

Koryszewska-Bagińska, A. et al. "Complete Genome Sequence of the Probiotic Strain *Lactobacillus casei* (Formerly *Lactobacillus paracasei*) LOCK919", *Genome Announcements*, Sep. 26, 2013, p. 1-2, vol. 1, Issue 5.

Koryszewska-Bagińska, A. et al. "Genome Sequence of the Probiotic Strain *Lactobacillus rhamnosus* (Formerly *Lactobacillus easei*) LOCK908", *Genome Announcements*, Feb. 20, 2014, pp. 1-2, vol. 2, Issue 1.

Maze, A. et al. "Complete Genome Sequence of the Probiotic *Lactobacillus casei* Strain BL23" *Journal of Bacteriology*, May 2010, pp. 2647-2648, vol. 192, No. 10.

Son, V.M. et al., "Dietary administration of the probiotic, *Lactobacillus plantarum*, enhanced the growth, innate immune responses, and disease resistance of the grouper *Epinephelus coioides*", *Fish & Shellfish Immunology*, 2009, pp. 691-698, vol. 26.

Van De Guchte, M. et al., "The complete genome sequence of *Lactobacillus bulgaricus* reveals extensive and ongoing reductive evolution" *PNAS*, Jun. 13, 2006, pp. 9274-9279, vol. 103, No. 24.

Wang, J. et al., "*Lactobacillus plantarum* ZLP001: In vitro Assessment of Antioxidant Capacity and Effect on Growth Performance and Antioxidant Status in Weaning Piglets" *Asian-Australian Journal of Animal Sciences*, Aug. 2012, pp. 1153-1158, vol. 25, No. 8.

Cao, W. et al. "Effects of Lactic Acid Bacteria on Growth Performance, Meat Quality and mRNA Relative Expression of Insulin-Like Growth Factor-1, Insulin-Like Growth Factor-1 Receptor and Growth Hormone Receptor in Muscle of Rex Rabbits" *Chinese Journal of Animal Nutrition*, pp. 2902-2910 (pp. 1-13 of English language translation), vol. 26, No. 9.

Schwarzer, M. et al. "*Lactobacillus plantarum* strain maintains growth of infant mice during chronic undernutrition" *Science*, Feb. 19, 2016, pp. 854-857, vol. 351, Issue 6275.

Schwarzer, M. et al. "Daily Administration of *Lactobacillus plantarum* Improves Mouse Juvenile Growth Kinetics by Sustaining Somatotropic Axis Activity Upon Undernutrition" *Journal of Canadian Association of Gastroenterology*, Feb. 2018, p. 445, vol. 1, Issue Supplement 2.

Zhang, C.-M. et al. "Effect of *Lactobacillus* on Productive Performance and Immunity of Weaned Piglets" *Journal of South China Agriculture University*, 2006, pp. 81-84 (pp. 1-9 of English language translation) No. 3.

Mohan, S. et al. "Role of Insulin-like Growth Factor-1 in the Regulation of Skeletal Growth" *Curr Osteoporos Rep.*, 2012, pp. 178-186, vol. 10.

\* cited by examiner

PROBIOTIC COMPOSITION MAKING IT POSSIBLE TO PROMOTE JUVENILE LIVESTOCK GROWTH

CROSS-REFERENCE TO RELATED APPLICATION

This application is the U.S. national stage application of International Patent Application No. PCT/EP2017/052982, filed Feb. 10, 2017.

The present invention relates to a probiotic composition for promoting juvenile growth in vertebrate livestock. It also relates to a probiotic composition for increasing the IGF-1 level in vertebrate livestock. This composition includes as active principle or ingredient at least one bacterium with intestinal tropism, preferably a lactic acid bacterium.

Described as "an additional organ", the intestinal microbial community (or intestinal microbiota) plays a key beneficial role for the host by performing many biological functions, such as aiding digestion efficiency, substrate metabolism, pathogen control, and immune response establishment and homeostasis.

Defined in 2001 by the World Health Organization (WHO) and the United Nations Food and Agriculture Organization (FAO), probiotics are "living microorganisms, which, when ingested in sufficient quantity, exert positive effects on health, beyond traditional nutritional effects".

WO2015173386 relates to a Lactobacillus composition for promoting human and animal juvenile growth in the case of malnutrition. However, in this context of nutritional deficiency, this composition, although improving juvenile growth, does not by itself fully restore optimal growth in undernourished subjects treated with this composition. Conversely, a Lactobacillus composition is not expected to have a significant effect on juvenile growth in animals fed a conventional diet.

Some livestock operators have turned to the administration of growth hormone or antibiotics to promote livestock growth. Work has also described the administration of probiotics to increase weight gain.

There is still a need for an effective solution for promoting livestock growth, which does not resort to the administration of hormone or growth factor or antibiotics, and which induces skeletal growth.

An objective of the invention is thus to propose a probiotic solution to this need, with compositions for promoting juvenile growth, namely weight and linear growth, in livestock fed a conventional diet, pre- and/or post-weaning, notably post-weaning.

Another objective of the invention is to promote IGF-1 production.

Another objective of the invention is to provide such compositions, based on the use of bacterial strains with intestinal tropism, notably commensal strains, or strains acceptable as probiotic.

Yet another objective of the invention is to provide such compositions promoting notably linear growth (also called skeletal growth, resulting from bone growth), weight gain in terms of muscle mass, increase in lean mass (primarily muscle mass and skeletal mass) and/or increase in bone length in animals.

Yet another objective of the invention is to provide such compositions and methods to support a health and/or nutritional claim in accordance with current legislation, including European legislation.

The invention is based on the fact that certain strains of bacteria with intestinal tropism in an animal species have an effect promoting juvenile growth in a subject of the same species or of another species which is fed a conventional rearing diet (animal fed according to current breeding practices providing a ration for balanced growth) for the animal species or the animal in question. It was thus shown that bacterial strains of the genus Lactobacillus were capable of promoting juvenile growth in a mouse model using a conventional breeding diet for mice, and, moreover, a link was established between these growth results in mice and an increase in the serum insulin—like growth factor 1 (IGF-1) level in mice treated under these conditions with these bacteria.

The invention thus relates to the use and the administration of bacterial strains with intestinal tropism, preferably a lactic acid bacterium, in particular of the genus Lactobacillus, in particular Lactobacillus plantarum, to promote juvenile growth in vertebrate livestock, in particular for post-weaning growth. The optimisation of juvenile growth or of post-weaning growth can be measured on various objective criteria taken individually or in combination. These objective criteria include in particular linear growth (length from the snout or muzzle or mouth to the base of the tail), weight gain, preferably linked to linear growth and/or an increase in muscle mass (the objective being to avoid weight gain due to increased fat mass), lean mass, which includes muscle mass and skeletal mass, bone length or body length for fish, the use according to the invention leading to an increase in one or more of the criteria observed. Advantageously, these criteria are accompanied by an increase in the serum IGF-1 level, exemplified below in mice. The criterion of increase in the serum IGF-1 level can be used alone, especially once correlated with the other criteria.

The present invention thus has as an object a probiotic composition or an animal feed, comprising at least one bacterial strain, in particular a lactic acid bacterium, promoting juvenile growth in a livestock animal, preferably with stimulation of juvenile growth, notably linear growth, and/or of the IGF-1 level. This composition is intended for use in promoting juvenile growth in a livestock animal.

The bacterium has "intestinal tropism", which means that the bacterium is able to pass the gastric barrier, either naturally or when administered in a gastro-protected formulation, and is able to persist in the intestine so as to produce an effect promoting juvenile growth.

According to an advantageous feature of the invention, the bacterium can promote IGF-1 production in animals treated with the composition in accordance with the invention. An increase in the IGF-1 level can notably be correlated with stimulated juvenile growth (qualifiable by the above-mentioned growth criteria). The invention thus relates to a probiotic composition for promoting or increasing IGF-1 production in juvenile animals treated with the composition in accordance with the invention.

The invention proposes in particular bacterial strains belonging to the following families: Lactobacillaceae, Streptococcaceae, Enterococcaceae, Leuconostocaceae, Bifidobacteriaceae. According to one mode, the invention uses one or more strains of the genus Lactobacillus, in particular of one of the following species: Lactobacillus delbrueckii, Lactobacillus plantarum, Lactobacillus fermentum, Lactobacillus casei, Lactobacillus paracasei, Lactobacillus rhamnosus.

More particularly, it is a matter of bacteria belonging to the species Lactobacillus plantarum, Lactobacillus fermentum, Lactobacillus casei, Lactobacillus paracasei, Lactobacillus rhamnosus. According to one mode, the strain is selected from the species *Lactobacillus plantarum, Lactobacillus fermentum, Lactobacillus casei*.

The invention notably has as an object a probiotic composition including at least one strain of *Lactobacillus delbrueckii, Lactobacillus plantarum, Lactobacillus fermentum, Lactobacillus casei* or *Lactobacillus paracasei*, with intestinal tropism, for use in promoting juvenile growth in vertebrate livestock fed a conventional rearing diet, with stimulation of linear growth and/or of IGF-1 level.

The invention also has as an object a probiotic composition comprising at least one lactic acid bacteria strain, preferably *Lactobacillus*, with intestinal tropism, for use in increasing the IGF-1 level in vertebrate livestock fed a conventional rearing diet.

According to an embodiment of the objects of the invention, the bacterial strain is selected from *L. plantarum* WJL, *L. plantarum* G821 (CNCM 1-4979), *L. plantarum* NIZO2877, *L. casei* ATCC 393, *L. casei* L919, *L. paracasei* ATCC25302, *L. paracasei* Shirota, *L. fermentum* ATCC9338, *L. rhamnosus* L900, *L. rhamnosus* L908, *L. rhamnosus* GG. According to one mode, the strain is selected from *L. plantarum* WJL, *L. plantarum* G821, *L. casei* ATCC 393, *L. casei* L919, *L. fermentum* ATCC9338.

In a specific embodiment, it is a matter of bacteria of the species *Lactobacillus plantarum*, for example strain WJL or strain G821, deposited with the Collection Nationale de Culture de Microorganismes (Pasteur Institute) under registration number CNCM 1-4979 on 11 May 2015. Strain G821 was obtained by experimental evolution (i.e., accumulation and selection of natural variants) of strain *L. plantarum* NIZO2877.

According to one mode, the compositions according to the invention comprises at least one bacterial strain selected from these groups, which has the required properties and promotes juvenile growth. Of course, the composition of the invention may comprise more than one bacterial strain meeting the needs of the invention. In particular, the composition comprises two or more of these bacterial strains, selected from the same species or from different species.

According to an advantageous embodiment, the bacterium is an *L. plantarum*. Suitable strains are *L. plantarum* G821, *L. plantarum* NIZO2877 and *L. plantarum* WJL (Eun-Kyoung Kim et al., Genome Announcements, November/December 2013, vol. 1, no. 6 e00937-13, GenBank AUTE00000000, *Lactobacillus plantarum* WJL, whole genome shotgun sequencing project). This strain WJL was initially isolated and can be isolated from drosophila (J H Ryu et al., Science 2008, 319:777-782).

Other examples of suitable strains are as follows: *L. casei* ATCC 393, *L. casei* L919 (Koryszewska-Baginska A. et al., 26 Sep. 2013, Genome Announc), *L. paracasei* ATCC25302, *L. paracasei* Shirota (Yuki N et al., Int J Food Microbiol. 1 Apr. 1999; 48(1):51-7), *L. fermentum* ATCC9338, *L. rhamnosus* L900 (Aleksandrzak-Piekarczyk T. et al., Genome Announc, 15 Aug. 2013), *L. rhamnosus* L908 (Koryszewska-Baginska A. et al., 20 Feb. 2014, Genome Announc), *L. rhamnosus* GG (Kankainen M. et al., Proc Natl Acad Sci USA, 6 October 2009).

The present invention thus contributes to the art the teaching that bacterial strains with intestinal tropism promote juvenile growth in animals raised on conventional diets. But the invention is not limited to this teaching; it also gives the skilled person the tools to reliably determine the bacterial strains useful for the invention. Different criteria can be used as a basis for testing, either alone or in combination. These criteria include the serum IGF-1 level in the animal model (e.g., mouse), mouse growth models illustrated, for example, by femur length or linear growth of the animals, or weight gain, notably linked to linear growth and/or to increase in muscle mass and/or to increase in lean mass. On the basis of these or similar criteria, it is possible for the skilled person to develop tests comparing individuals raised in the presence or in the absence of the bacterium to be tested.

An organism (e.g., mouse) raised in an environment free of microorganisms and thus free of intestinal flora is referred to as an "axenic" organism.

An associated axenic organism (e.g., mouse) raised in the presence of a single microorganism and thus carrying this single microorganism as intestinal flora is referred to as a "monoxenic" organism.

According to the invention, it is possible to determine whether a bacterial strain with intestinal tropism can promote growth in the case of a conventional diet, by using an axenic mouse model that allows linear growth monitoring of mice in the presence of the bacterium to be tested in comparison with the absence of microbiota and/or with the presence of a reference bacterial strain. This model can be used as a first-line approach.

According to a feature of the invention, the bacterial strains of the invention are characterised by the fact that they respond positively to the following linear growth test:

from the same mouse line (typically Balb/c mice), a line of axenic parent mice and a line of monoxenic parent mice (associated with the bacterium to be tested) are established, and juveniles are produced which are raised with the parents on a conventional diet comprising about 40% carbohydrates, about 25% proteins and about 9% lipids, until they are weaned (on day 21); to form the group of monoxenic juveniles, parents mono-associated with the bacterial strain to be tested are used, on day 21: 8 weaned juveniles from each of these two lines are available, forming the monoxenic group and the axenic group, and they are raised on a conventional diet comprising about 40% carbohydrates, about 25% proteins and about 9% lipids, on day 56: the mean size of the mice is determined for the group in question by measuring from the tip of the nose to the base of the tail of each individual; another possible measurement consists in sacrificing the individuals, removing the femurs and measuring their length, the lactic acid bacteria strain being considered to respond positively to the test if the mean individual size and/or the mean femur length of the monoxenic group are/is greater, respectively, than the mean individual size and/or femur length of the axenic group, with a p-value of less than 0.05, in Tukey's statistical test.

The present invention thus has as an object a composition comprises at least one bacterial strain with intestinal tropism, in particular a lactic acid bacterium, for use in promoting juvenile growth in a context of a conventional diet, in which the bacterial strain responds positively to the linear growth test in mice. By way of example, the following strain may be cited: *L. plantarum* WJL. Other strains can be identified among bacteria with intestinal tropism and notably among the species and strains mentioned above, notably among strains *L. plantarum* G821, *L. casei* ATCC 393, *L. casei* L919, *L. paracasei* ATCC25302, *L. paracasei* Shirota, *L. fermentum* ATCC9338, *L. rhamnosus* L900, *L. rhamnosus* L908, *L. rhamnosus* GG.

In an embodiment of the invention, strain WJL or another strain with a "marked" effect is used as reference strain in order to identify and select bacterial strains having a "marked" effect on juvenile growth, namely an effect close to that of said reference strain, e.g. WJL (effect not significantly different from the reference strain, e.g. WJL), or a "strong" effect on juvenile growth (effect significantly greater than the reference strain, e.g. WJL).

To this end, the mouse test (including 8 mice per condition) is applied to the reference strain, e.g. WJL, and to the strain to be tested (preferably in parallel, or else it is possible to use reference data generated beforehand for strain WJL, for example the data presented in the examples). The mean values obtained for the two strains are then compared. The bacterial strain tested is considered to be a strain with a marked effect if the mean of the size of the individuals and/or of the length of the femurs of the monoxenic group is not significantly different from the corresponding mean for the reference group, e.g. WJL, with a p-value of greater than 0.05 in Tukey's statistical test. The effect is strong if said mean for the strain to be tested is significantly greater than the mean for the reference strain, e.g. WJL, which is the case when the p-value of the statistical test is less than 0.05. The effect is described as intermediate if said mean for the strain to be tested (which was described relative to the axenic mice in the preceding test) is significantly lower than the mean for the reference strain, e.g. WJL, which is the case when the p-value of the statistical test is less than 0.05.

The composition of the invention will preferably comprise at least one bacterial strain having such a marked or strong effect.

The bacterial strains of the invention can be characterised by the fact that they have a positive impact on the serum IGF-1 level. It was therefore possible, on the basis of an axenic mouse model, to show that mice raised on a conventional diet and in the presence of the bacterium (monoxenic mice) had higher growth and, at the same time, a higher serum IGF-1 level, compared to these same mice raised with this conventional diet, but in the absence of the bacterium (axenic mice). This makes it possible to propose a test to determine whether a bacterial strain has the potential to increase the serum IGF-1 level, said test which potentially can be applied in combination with a linear growth test in order to clarify or to refine the effect of the strain on growth.

In this case, the bacterial strains of the invention are characterised by the fact that they respond positively to the following serum IGF-1 level test:

from the same mouse line (typically Balb/c mice) a line of axenic parent mice and a line of monoxenic parent mice (associated with the bacterium to be tested) are established, and juveniles are produced which are raised with the parents on a conventional diet of about 40% carbohydrates, about 25% proteins and about 9% lipids until they are weaned (on day 21); to form the group of monoxenic juveniles, parents mono-associated with the bacterial strain to be tested are used, on day 21: 8 weaned juveniles from each of these two lines are available, forming the monoxenic group and the axenic group, and they are raised on a conventional diet comprising about 40% carbohydrates, about 25% proteins and about 9% lipids, on day 56: blood is drawn from the juveniles of each group and the mean serum IGF-1 level is determined for each group; this measurement of the serum IGF-1 level is preferably performed on diluted serum (1:25); commercial ELISA kits for detecting IGF-1 are preferably used, following the manufacturer's instructions, the lactic acid bacteria strain is considered to respond positively to the test if the mean serum IGF-1 level of the monoxenic group is higher than the mean serum level of the axenic group with a p-value of less than 0.05 in Tukey's statistical test.

The present invention thus has as an object a composition comprising at least one bacterial strain with intestinal tropism, in particular a lactic acid bacterium, for use in promoting juvenile growth under a conventional diet, in which the bacterial strain increases the serum IGF-1 level. It is notably a bacterial strain that responds positively to the IGF-1 test in mice as described above.

The present invention also has as an object a composition comprising at least one bacterial strain with intestinal tropism, in particular a lactic acid bacterium, for use in promoting juvenile growth under a conventional diet, in which the bacterial strain responds positively to the linear growth test in mice and increases the serum IGF-1 level in these same mice. It is notably a bacterial strain that responds positively to the linear growth and IGF-1 tests in mice as described above.

By way of example, the following strain may be cited: *L. plantarum* WJL. Other strains can be identified among the bacteria with intestinal tropism and notably among the species and strains mentioned above, notably among strains *L. plantarum* G821, *L. casei* ATCC 393, *L. casei* L919, *L. paracasei* ATCC25302, *L. paracasei* Shirota, *L. fermentum* ATCC9338, *L. rhamnosus* L900, *L. rhamnosus* L908, *L. rhamnosus* GG.

In an embodiment of the invention, strain WJL or another strain with a "marked" effect is used as reference strain in order to identify and select bacterial strains having a "marked" effect on the serum IGF-1 level, namely an effect close to that of said reference strain, e.g. WJL (effect not significantly different from the reference strain, e.g. WJL), or a "strong" effect on the serum IGF-1 level (effect significantly greater than the reference strain, e.g. WJL).

To this end, the mouse test (including 8 mice per condition) for measuring the serum IGF-1 level is applied to the reference strain, e.g. WJL, and to the strain to be tested (preferably in parallel, or else it is possible to use reference data generated beforehand for the reference strain, e.g. WJL, for example the data presented in the examples). The mean serum IGF-1 levels obtained for the two strains are then compared. The bacterial strain tested is considered to be a strain with a marked effect if the mean IGF-1 level of the monoxenic group is not significantly different from the mean for the reference group, e.g. WJL, with a p-value of greater than 0.05, in Tukey's statistical test. The effect is strong if said mean for the strain to be tested is significantly greater than the mean for the reference strain, e.g. WJL, when the p-value is less than 0.05. The effect is described as intermediate if said mean for the strain to be tested (described beforehand on the preceding axenic test) is significantly lower than the mean for the reference strain, e.g. WJL, when the p-value is less than 0.05.

The composition of the invention will thus preferably comprise a bacterial strain having such a marked or strong effect, and in particular said bacterial strain has a marked or strong effect both on linear growth and on the serum IGF-1 level.

The composition can be used in domesticated animals in the broad sense, notably including grazing animals (livestock), farmyard animals, aquatic animals, pets. In particular, the composition can be used on mammals, in particular production animals (cattle, sheep, goats, pigs, fowl), pets (dogs, cats) and sporting animals (horses, dromedaries, camels), preferably between weaning and sexual maturity, or between weaning and the adult stage (characterised by reaching adult size, end of skeletal growth), referred to herein as juvenile animals. The composition can be administered to castrated animals, notably before castration and/or in the remaining post-castration period of skeletal growth. It can also be used in fish farming. In an embodiment, the animal is a carnivore. In another embodiment, the animal is a ruminant.

The composition can notably contain an amount of about $10^5$ to about $10^{12}$, notably of about $10^6$ to about $10^{12}$, preferably of about $10^8$ to about $10^{12}$ colony-forming bacterial cells (CFU) according to the invention, per gram of composition. CFU stands for the English technical expression "colony-forming units". "Per gram of composition" is preferably understood to mean the probiotic composition consisting of bacteria, co-ingredients, and excipients or vectors. "Bacterial cells" is understood to mean a single strain of bacterium in accordance with the invention or a mixture of at least two bacteria, in accordance with the invention.

The composition can notably comprise the one or more lactic acid bacteria in live form. The composition can be in a ready-to-use form or in a form to be mixed or diluted with a food, an excipient or a liquid food such as drinking water.

It can be a bacterial suspension, which can be frozen and thawed before use.

It can be a lyophilised powder, which can be used as such, in powder, granule, tablet, bolus, hard capsule or soft capsule form, or used after incorporation in a suitable vehicle. This composition can comprise a conventional lyophilisation excipient.

The composition can be an oral administration form (for example powder, soft capsule, tablet, bolus) in a gastro-protected form so as to pass through the stomach and release the bacteria in the intestine.

According to an embodiment, the composition is a solid composition, e.g. tablet, bolus, soft capsule, hard capsule, gastro-protected so as to pass through the stomach and release the bacteria in the intestine. According to one mode, the form, notably granules, can be used as feed in aqueous medium, notably for fish.

According to an embodiment, the composition is a liquid or is to be dissolved in a liquid or to be suspended in a liquid, for example drinking water; in this case the composition is initially solid, e.g. powder, granule, dissolvable tablet, for example effervescent tablet, or deliquescent tablet in the liquid.

According to an embodiment, the composition is solid, e.g. powder, granule, tablet, bolus, and intended or suitable for mixing with food.

According to an embodiment, the composition is solid, in a ready-to-use form without the need for mixing with food, but can nevertheless be mixed with food, for example a palatable tablet or bolus.

The invention also has as an object a food for animal-breeding containing at least one bacterium or composition of the invention. By way of example, the food comprises the composition of the invention mixed with at least carbohydrates, proteins and lipids. The food can be in a liquid, emulsion or solid form, and among the solid forms mention may be made, by way of example, of granules, boluses, flakes, silage added to the composition, fodder added to the composition. In particular, the food can be a complete food, a functional food, a milk replacer, a formulated food, a concentrated supplement.

The invention also has as an object a probiotic treatment method for promoting juvenile growth in livestock, comprising the administration to an animal according to the invention of a composition according to the invention. Preferably, the composition is administered via the oral route. Preferably, the composition is administered several times during a period ranging from weaning to sexual maturity.

The invention also has as an object the animal-breeding method integrating said probiotic treatment.

Said probiotic treatment or breeding method comprises the administration of a sufficient amount of a composition as described above to the young animal, preferably post-weaning. The method will comprise one or more administrations, which can be spread over the growth period of the subject (until sexual maturity), of doses of the composition of the invention. The doses can be divided to facilitate administration. The frequency of administration is notably between one dose (single or divided) every day and one dose every month. Typically, the frequency of administration will be between one dose (single or divided) every day and one dose every week, or even every 2, 3, 4, 5 or 6 days. Each dose (single or divided) notably represents several grams to several tens of grams of composition.

The method notably comprises the administration of a composition comprising an amount of about $10^5$ to about $10^{12}$, in particular of about $10^6$ to about $10^{12}$, preferably of about $10^8$ to about $10^{12}$ colony-forming bacterial cells (CFU) per gram of composition ("bacterial cells" means a single strain of bacterium in accordance with the invention or a mixture of at least two bacteria in accordance with the invention).

The method preferably comprises the administration of a composition comprising the one or more lactic acid bacteria in live form.

The form of the composition can be solid or liquid and take any of the forms presented above.

In an embodiment, the composition of the invention, notably the composition used in the treatment method, comprises at least one bacterial strain that is not naturally occurring in the treated species. In this configuration, when there are several different bacteria, it is sufficient that one of them is not naturally occurring. On the other hand, this bacterium will have intestinal tropism in the animal species and meet the definition of active strains according to the invention.

The invention also relates to a method for screening bacteria capable of promoting juvenile growth under a conventional diet, using an axenic mouse model.

The method includes the following steps:
juveniles are provided from two lines derived from the same mouse strain (typically Balb/c mice), namely a line of axenic parent mice and a line of monoxenic parent mice (associated with the bacterium to be tested),
they are raised on a conventional diet comprising about 40% carbohydrates, about 25% proteins and about 9% lipids,
at the end of a suitable rearing period, the mean value of one or more parameters is determined for each group, said parameters being related to growth (for example weight gain, linear growth for example by measuring the size of the individuals or the length of their femurs), and/or to the serum IGF-1 level,
the lactic acid bacteria strain is considered to respond positively to the test if the mean value of the parameter measured in the monoxenic group is higher than the mean value of the parameter measured in the axenic group with a p-value of less than 0.05 in Tukey's statistical test.

Preferably, the screening method adopts the features of the mouse test of linear growth or of serum IGF-1 level described above.

The screening method can also be a comparative test with a reference strain, for example strain WJL, and this test thus adopts the features described above for the mouse tests.

The various tests described are quite capable of being performed with a different diet, as long as it is a diet suitable for mice.

The invention will now be described in greater detail using embodiments of the invention taken as non-limiting examples.

The male offspring (minimum 8 individuals) of three groups of individuals from the same colony of axenic mice were studied, the first group consisting of axenic juveniles (germ-free (GF) group), the second of juveniles from parents mono-associated with strain *L. plantarum* WJL (WJL group), and the third of juveniles from parents mono-associated with strain *L. plantarum* NIZO2877 (NIZO2877 group). The parents and juveniles are raised on a conventional diet (40% carbohydrates, 25.1% proteins, 9.1% lipids and 3646 kcal/kg) until the juveniles are weaned (day 21 post-birth), then the weaned juveniles are raised on a conventional diet until day 56.

Four parameters illustrating the juvenile growth of these individuals were studied: the primary parameter being linear growth or size increase (measured from the nose to the base of the tail) for a period of 35 days following weaning (days 21 to 56), then three secondary parameters, namely (1) weight gain for a period of 35 days following weaning (days 21 to 56), (2) femur length of a set of individuals (at least 8 individuals) representative of the population tested on day 56, and finally (3) the serum level on day 56 of growth factor IGF-1 in at least 8 individuals.

Statistical analyses were performed using the t-test with the GraphPad software (GraphPad PRISM 5.04, San Diego, USA); values of $p<0.05$ are considered significant.

(1) Weight and Size Increase:

The mice were anaesthetised by brief exposure to isoflurane in order to measure their weight and size (from the nose to the base of the tail) on day 21 and day 56.

TABLE 1

Weight gain, days 21-56, in g/day

| | GF | Lp WJL | Lp NIZO2877 |
|---|---|---|---|
| | 0.272286 | 0.357619 | 0.319337 |
| | 0.231714 | 0.369333 | 0.353623 |
| | 0.242857 | 0.353333 | 0.31648 |
| | 0.34 | 0.341905 | 0.291051 |
| | 0.263429 | 0.343333 | 0.283623 |
| | 0.311429 | 0.359048 | 0.250765 |
| | 0.331429 | 0.293333 | 0.276765 |
| | 0.322857 | 0.301905 | 0.385051 |
| | 0.308571 | | 0.345051 |
| | | | 0.345051 |
| | | | 0.373623 |
| | | | 0.327908 |
| Mean | 0.291619111 | 0.339976125 | 0.322360667 |
| Standard error of the mean | 0.01328949 | 0.009779005 | 0.011782513 |
| Standard deviation | 0.03986847 | 0.027659203 | 0.040815822 |

TABLE 1-continued

Weight gain, days 21-56, in g/day t-test for unpaired series

| Lp WJL vs. GF | $p = 0.0118$ |
|---|---|
| Lp WJL vs. Lp NIZO2877 | $p = 0.3014$ |
| Lp NIZO2877 vs. GF | $p = 0.1008$ |

Lp = *L. plantarum*

TABLE 2

Size increase, days 21-56, in cm/day

| | GF | Lp WJL | Lp NIZO2877 |
|---|---|---|---|
| | 0.054286 | 0.072508 | 0.056122 |
| | 0.062857 | 0.063937 | 0.061837 |
| | 0.057143 | 0.075365 | 0.061837 |
| | 0.06 | 0.078222 | 0.061837 |
| | 0.054286 | 0.069651 | 0.056122 |
| | 0.057143 | 0.081079 | 0.05898 |
| | 0.057143 | 0.063937 | 0.05898 |
| | 0.06 | 0.066794 | 0.05898 |
| | 0.048571 | | 0.061837 |
| | | | 0.067551 |
| | | | 0.073265 |
| | | | 0.061837 |
| Mean | 0.056825444 | 0.071436625 | 0.06159875 |
| Standard error of the mean | 0.001383791 | 0.002286716 | 0.001382733 |
| Standard deviation | 0.004151373 | 0.006467809 | 0.004789929 | t-test for unpaired series

| Lp WJL vs. GF | $p < 0.0001$ |
|---|---|
| Lp WJL vs. Lp NIZO2877 | $p = 0.0010$ |
| Lp NIZO2877 vs. GF | $p = 0.0275$ |

(2) Femur Length:

The mice are sacrificed on day 56; a femur is removed and stripped of muscle and its length is measured with a Vernier caliper.

TABLE 3

Femur length in mm on day 56

| | GF | Lp WJL | Lp NIZO2877 |
|---|---|---|---|
| | 13 | 13.7 | 13.2 |
| | 13.1 | 13.8 | 13.3 |
| | 13.1 | 13.6 | 13.4 |
| | 13.3 | 13.8 | 13.2 |
| | 13.7 | 13.5 | 13.2 |
| | 13.5 | 13.8 | 13.6 |
| | 13.5 | 13.5 | 13.3 |
| | 13.7 | 13.6 | 13.6 |
| | | | 13.8 |
| | | | 13.6 |
| | | | 14 |
| | | | 13.5 |
| Mean | 13.3625 | 13.6625 | 13.475 |
| Standard error of the mean | 0.09808433 | 0.046049275 | 0.073983004 |
| Standard deviation | 0.277424378 | 0.130247018 | 0.256284643 |

TABLE 3-continued

Femur length in mm on day 56 t-test for unpaired series

| | |
|---|---|
| Lp WJL vs. GF | p = 0.0151 |
| Lp WJL vs. Lp NIZO2877 | p = 0.0735 |
| Lp NIZO2877 vs. GF | p = 0.3641 |

(3) Serum IGF-1 Levels:

IGF-1 levels are measured on serum obtained from the blood of mice sacrificed on day 56. The measurement is performed on diluted serum (1:25) using the ELISA Ready-SET-Go Kit (eBioscience, USA), following the manufacturer's instructions.

TABLE 4

IGF-1 level in ng/mL on day 56

| GF | Lp WJL | Lp NIZO2877 |
|---|---|---|
| 67.2375 | 45.51875 | 69.89375 |
| 44.83125 | 79.70625 | 61.3 |
| 47.6125 | 71.6125 | 42.39375 |
| 42.4875 | 72.425 | 48.55 |
| 39.3 | 38.55 | 39.55 |
| 44.01875 | 40.425 | 31.8 |
| 42.1125 | 59.175 | 53.45625 |
| 39.3 | 47.76875 | 51.4875 |
| 41.32248 | | 41.14375 |
| 50.11075 | | 40.3 |
| 34.41869 | | 26.7375 |
| 31.5581 | | 34.39375 |
| 41.00821 | | |

TABLE 4-continued

IGF-1 level in ng/mL on day 56

| | | | |
|---|---|---|---|
| Mean | 43.48601769 | 56.89765625 | 45.08385417 |
| Standard error of the mean | 2.402432601 | 5.675518549 | 3.594197638 |
| Standard deviation | 8.662093929 | 16.05279061 | 12.45066584 | t-test for unpaired series

| | |
|---|---|
| Lp WJL vs. GF | p = 0.0217 |
| Lp WJL vs. Lp NIZO2877 | p = 0.0802 |
| Lp NIZO2877 vs. GF | p = 0.7111 |

The results illustrate a "marked" effect of strain *L. plantarum* WJL on linear growth (higher mean value and value of $p<0.05$ compared to the axenic condition) and an "intermediate" effect of strain *L. plantarum* NIZO2877 (higher mean value and value of $p<0.05$ compared to the axenic condition and lower mean value and value of $p<0.05$ compared to the *L. plantarum* WJL condition). The effect of strain *L. plantarum* WJL is confirmed with the secondary parameters, namely weight gain, IGF-1 level and femur length compared to the axenic condition (higher mean value and value of $p<0.05$). However the intermediate effect of strain *L. plantarum* NIZO2877 is not confirmed on the secondary parameters of the study. The secondary parameters cannot therefore be used to identify the quantitative effect of the strain tested; only the primary parameter (linear growth) makes this possible.

All these results demonstrate, by scientific evidence, the juvenile growth-promoting effect of certain *Lactobacillus* strains and exemplify a "marked" effect or a "moderate" effect of certain strains on linear growth. A "strong" effect will be obtained with certain strains, said strong effect corresponding to a higher mean linear growth value and a value of $p<0.05$ compared to the *L. plantarum* WJL condition.

Strains are available at the ATCC, the Pasteur Institute of Paris, the Pasteur Institute of Lille, or published in the scientific literature and available from the principal investigators of the publications mentioned:

| | Public collection and/or publication with genome sequence |
|---|---|
| *Lactobacillus plantarum* WJL | Kim et al., Genome Announc. 21 Nov. 2013, 1(6).Pil: e00937-13 |
| *Lactobacillus plantarum* NIZO2877 | NIZO (2877) |
| *Lactobacillus casei* ATCC 393 | ATCC (393) |
| *Lactobacillus fermentum* ATCC 9338 | ATCC (9338) |
| *Lactobacillus fermentum* KLD | Pasteur Institute of Lille (A5.20) |
| *Lactobacillus fermentum* LMG | Pasteur Institute of Lille (A5.16) |
| *Lactobacillus paracasei* ATCC 25302 | ATCC (25302) |
| *Lactobacillus paracasei* BL23 | Pasteur Institute of Lille (A3.6) and Mazé et al., J. Bacteriol., May 2010; 192(10): 2647-8 |
| *Lactobacillus paracasei* Shirota | |
| *Lactobacillus delbrueckii* spp. *bulgaricus* | Pasteur Institute of Lille (A3.5) |
| *Lactobacillus casei* L919 | ATCC (11842) and van de Guchte M, et al., Proc. Natl Acad Sci USA 13 Jun. 2006 |
| *Lactobacillus rhamnosus* L900 | |
| *Lactobacillus rhamnosus* L908 | Koryszewska-Baginska A et al., Genome Announc, 26 Sep. 2013 |
| *Lactobacillus rhamnosus* GG | Aleksandrzak-Piekarczyk T et al. Genome Announc, 15 Aug. 2013 |
| *Lactobacillus plantarum* G821 | Koryszewska-Baginska A et al. Genome Announc, 20 Feb. 2014 |
| | ATCC (53103) and Kankainen M et al., Proc Natl Acad Sci USA, 6 Oct. 2009 |
| | CNCM I-4979 |

The invention claimed is:

1. A method for promoting juvenile livestock growth with stimulation of the linear growth and/or of IGF-1 levels of animals fed a conventional rearing diet, comprising the administration of a composition or a food comprising at least several grams of a probiotic composition comprising about $10^5$ to about $10^{12}$ colony forming units (CFU) *Lactobacillus plantarum* WJL per gram of probiotic composition to said animal in an amount that promotes juvenile livestock growth with stimulation of the linear growth and/or of IGF-1 levels.

2. The method of claim 1, said method promoting juvenile livestock post-weaning growth.

3. The method of claim 1, wherein the animal is post-weaning livestock.

4. The method of claim 1, said method further comprising measuring serum insulin-like growth factor 1 (IGF-1) levels to determine an increase of IGF-1 levels in treated animals.

5. The method of claim 1, said method stimulating linear growth.

6. The method of claim 1, said method increasing levels of IGF-1.

7. A method of promoting juvenile livestock growth with stimulation of the linear growth and/or of IGF-1 levels of animals fed a conventional rearing diet, comprising the administration of a composition or a food comprising at least several grams of a probiotic composition comprising about $10^5$ to about $10^{12}$ colony forming units (CFU) *Lactobacillus plantarum* WJL per gram of probiotic composition to said animal, wherein the probiotic composition is administered once a day in an amount that promotes juvenile livestock growth with stimulation of the linear growth and/or of IGF-1 levels.

8. A method of promoting juvenile livestock growth with stimulation of the linear growth and/or of the IGF-1 level of animals fed a conventional rearing diet, comprising the administration of a composition or a food comprising at least several grams of a probiotic composition comprising live bacteria in an amount of about $10^5$ to about $10^{12}$ colony forming units (CFU) *Lactobacillus plantarum* WJL per gram of probiotic composition to said animal in an amount that promotes juvenile livestock growth with stimulation of the linear growth and/or of IGF-1 levels.

9. The method of claim 1, wherein said probiotic composition is administered at a frequency of once per day to once per week.

10. The method of claim 9, wherein said probiotic composition is administered at a frequency of once per day for three to five days each week.

11. The method of claim 1, said method comprising the administration of a composition or a food comprising several grams to several tens of grams of a probiotic composition comprising about $10^5$ to about $10^{12}$ CFU *Lactobacillus plantarum* WJL per gram of probiotic composition to said animal in an amount that promotes juvenile livestock growth with stimulation of the linear growth and/or of IGF-1 levels.

12. The method of claim 7, said method comprising the administration of a composition or a food comprising several grams to several tens of grams of a probiotic composition comprising about $10^5$ to about $10^{12}$ CFU *Lactobacillus plantarum* WJL per gram of probiotic composition to said animal, wherein the probiotic composition is administered once a day in an amount that promotes juvenile livestock growth with stimulation of the linear growth and/or of IGF-1 levels.

13. The method of claim 8, said method comprising the administration of a composition or a food comprising several grams to several tens of grams of a probiotic composition comprising live bacteria in an amount of about $10^5$ to about $10^{12}$ CFU *Lactobacillus plantarum* WJL per gram of probiotic composition to said animal in an amount that promotes juvenile livestock growth with stimulation of the linear growth and/or of IGF-1 levels.

* * * * *